United States Patent
Schaefer

(10) Patent No.: US 9,180,241 B2
(45) Date of Patent: Nov. 10, 2015

(54) TUBE ROLLER PUMP INCLUDING PIVOTING COVER AND MEDICAL DEVICE FOR EXTRACORPOREAL BLOOD TREATMENT

(71) Applicant: B. Braun Avitum AG, Melsungen (DE)

(72) Inventor: Oliver Schaefer, Neuenstein (DE)

(73) Assignee: B. Braun Avitum AG, Melsungen (DE)

( * ) Notice: Subject to any disclaimer, the term of this patent is extended or adjusted under 35 U.S.C. 154(b) by 359 days.

(21) Appl. No.: 13/934,447

(22) Filed: Jul. 3, 2013

(65) Prior Publication Data

US 2014/0012202 A1    Jan. 9, 2014

(30) Foreign Application Priority Data

Jul. 3, 2012 (DE) .......................... 10 2012 105 919

(51) Int. Cl.
*A61M 37/00* (2006.01)
*A61M 1/30* (2006.01)
*F04B 43/12* (2006.01)

(52) U.S. Cl.
CPC .............. *A61M 1/30* (2013.01); *F04B 43/1253* (2013.01)

(58) Field of Classification Search
CPC . A61M 5/14242–5/14232; A61M 1/30–1/308; F04B 43/12–43/1292
USPC ....................... 604/4.01–6.16; 417/476–477.6
See application file for complete search history.

(56) References Cited

U.S. PATENT DOCUMENTS

| | | | |
|---|---|---|---|
| 4,798,580 A | 1/1989 | DeMeo et al. | |
| 5,588,815 A | 12/1996 | Zaleski, II | |
| 6,077,246 A | 6/2000 | Kullas et al. | |
| 6,203,528 B1 | 3/2001 | Deckert et al. | |
| 2013/0045121 A1* | 2/2013 | Rodau ............... | A61M 5/14232 417/477.6 |

FOREIGN PATENT DOCUMENTS

| | | |
|---|---|---|
| DE | 38 72 053 | 2/1993 |
| DE | 696 15 633 | 6/2002 |
| JP | 2008000425 | 1/2008 |
| WO | WO 2011/107326 | 9/2011 |

OTHER PUBLICATIONS

German Search Report for DE 10 2012 105 919.5 dated Jan. 16, 2013.
European Search Report for EP13174610.9 dated Oct. 21, 2013.

* cited by examiner

*Primary Examiner* — Philip R Wiest
(74) *Attorney, Agent, or Firm* — RatnerPrestia

(57) ABSTRACT

Tube roller pumps for a medical device for extracorporeal blood treatment are disclosed. The pumps include a pump housing having a bearing surface and a rotor inside the bearing surface, wherein a tube is introduced between the bearing surface and the rotor in loop shape. Means for mounting the tubing segment are provided so the tubing segment can be pivot by pivoting a tilting element on which the tubing segment is at least partly mounted. A cover is mounted on the pump housing so that when closed upon pivoting the tubing segment toward the closed cover it constitutes a counter-bearing for the tilting element by which the tubing segment can be aligned with the pump housing. Means for automated unthreading of the tubing segment from the bearing are also included. Medical devices for extracorporeal blood treatment including the tube roller pump are also disclosed.

14 Claims, 8 Drawing Sheets

TUBE ROLLER PUMP INCLUDING PIVOTING COVER AND MEDICAL DEVICE FOR EXTRACORPOREAL BLOOD TREATMENT

CROSS REFERENCE TO RELATED APPLICATIONS

This application claims priority to German Patent Application No. DE 10 2012 105 919.5 filed Jul. 3, 2012, the contents of such application being incorporated by reference herein.

FIELD OF THE INVENTION

The invention relates to a tube roller pump for a medical device for extracorporeal blood treatment comprising a pump housing having a bent bearing surface and a rotor rotatable inside the bearing surface, a tubing segment being adapted to be introduced between the bearing surface and the rotor in loop shape and at the pump housing means for disposing the tubing segment being provided by which at least one end of the tubing segment can be arranged to be pivoting about an axis of rotation at the pump housing. The tubing segment can be pivoted by pivoting a tilting element on which the tubing segment is at least partly disposed.

The invention further relates to a medical device for extracorporeal blood treatment comprising such tube roller pump.

BACKGROUND SUMMARY

In medical devices for extracorporeal blood treatment (dialysis) frequently tube roller pumps are used for feeding the collected blood of the patient to a dialyser and back to the patient. The tube roller pumps function as peristaltic pumps, wherein a loop-shaped tubing segment is adjacent to an appropriately bent bearing surface of the pump housing. A rotor of the pump located inside the bearing surface then moves with its outer edges along the tubing segment, wherein it locally impresses the tube and thus enables feeding of blood through the tubing segment by the elastic material properties of the tubing segment. For this purpose, the blood is fed to the tubing segment via a first port and is discharged again via another port at the other end of the tubing segment.

The tubing segment thus forms a transfer system, as it is called, e.g. together with the feeding and discharging lines and several air traps, by which transfer system the blood of the patient is fed to a dialyser and back to the patient. Those transfer systems are preferably exchanged after each treatment and are not re-used for other patients. A used tubing segment thus has to be removed from the pump before a new transfer system is introduced into the device. For facilitating the handling during removal and rigging of the transfer system it is further known to provide a connector adapted to be connected to a feeding and discharging line, respectively, at each of the two ends of the tubing segment.

For accommodating a tube inside a roller pump the U.S. Pat. No. 8,047,819 B2, for example, describes holding means that are detachably mounted on the pump housing. So for different sizes and types of tubes different holding means can be mounted on the pump. A holding means includes a clamping device including at least one pivotable clamp jaw having a semicircular recess so that a tube can be held in the semicircular recess and in an opposed equally semicircular recess of another clamp jaw. The clamp jaws can also include plural of the recesses so that plural tubes can be simultaneously accommodated.

Moreover automatic systems are known that are intended to take over and thus facilitate threading and unthreading of the tube into the pump. Frequently, for unthreading an actuator moving the system from its therapy position into an unthreading position via a linear drive, for instance, has to be operated. For this purpose, it can be required in those systems to operate a switch/button at the medical device or to touch a software button on user interface.

Furthermore, multi-connectors are known which combine both ports for feeding and discharging lines in one component part which then can be introduced into a receiving portion of the pump housing. Via the geometric shape of such multi-connectors it is also possible to detect the presence thereof in the pump by the fact that during the inserting operation for instance a cylindrical portion of the multi-connector operates a plunger the axial position of which is queried via a light barrier. At the same time the plunger is part of an electromechanical actuator mounted in the pump housing which is adapted to eject the multi-connector via a linear drive.

In order to move a tubing segment at a tube roller pump into the respective threading and unthreading position, e.g. from JP 2008-000425 several variants of a pivoting member or rocker arm are known to which both ends of the loop-shaped tubing segment can be mounted. In a first pivoting position of the rocker arm the tubing segment then is provided in a position in which the threading operation can be started while the tubing segment can be unthreaded in a different pivoting position. The automatic threading and unthreading operation is performed by guide pins at the periphery of the rotor, the guide pins pressing the tube into or out of the pump housing upon rotation of the rotor.

During therapy and preferably also during automated threading and unthreading operations the pump is usually covered by a pivoting cover adapted to be manually closed and opened by the operator. The cover in this way constitutes a protection against intervention to prevent interventions with the pump during the motor-driven rotation of the rotor which might entail injuries and damages of the pump.

SUMMARY OF THE INVENTION

It is an object of the invention to provide a tube roller pump for a medical device for extracorporeal blood treatment comprising a cover which, in addition to the function of a protection against intervention, also assists mounting of a tubing segment and automated threading and unthreading operations.

Furthermore, it is an object of the invention to provide a medical device for extracorporeal blood treatment comprising such tube roller pump.

The tube roller pump according to aspects of the invention is suited for a medical device for extracorporeal blood treatment and includes a pump housing having a bent bearing surface and a rotor rotatable inside the bearing surface, wherein a tubing segment can be introduced between the bearing surface and the rotor in loop shape and at the pump housing means for detachably arranging and for maintaining the tubing segment are provided by which at least a portion or an end portion of the tubing segment can be pivoted about an axis of rotation with respect to the pump housing. Pivoting of the tubing segment can be carried out by pivoting a tilting element to which the tubing segment is at least partially attached or which holds part of the tubing segment, respectively.

According to aspects of the invention, the tube roller pump includes a cover pivoted to the pump housing by which the pump housing can be covered at least partially, the cover being formed and arranged on the pump housing so that in the closed state upon pivoting the tubing segment in the direction of the closed cover it forms a counter-bearing for the tilting element by which the tubing segment arranged thereon can be aligned at a defined position facing the pump housing. Furthermore, the tube roller pump includes at least means for automated unthreading of the tubing segment from the bearing surface at the defined position.

Apart from the mere function as protection against intervention, the pump according to aspects of the invention thus includes a cover which also assists the arrangement of the tubing segment and at least the automated unthreading operation, as in the closed state it forms a counter-bearing against which a tilting element can be pulled to bring the tubing segment into a defined unthreading position. The cover thus serves as a stop and moreover provides space for pivoting the tilting element.

In the closed position the cover enables the tilting element and a part of the tubing segment held in the same to be pivoted. The cover can be configured so that in the closed state the cover defines a pivoting space that substantially allows for only a particular and desired pivoting motion of the tilting element between a threading position and an unthreading position of the tubing segment.

The tilting element can have various designs. For example, the tilting element can be a fixed component of the tube roller pump and can have means for detachably arranging at least one end of the tubing segment. Both ends of the tubing segment then can be arranged temporarily at the tilting element and the position thereof can be varied by pivoting the tilting element about an axis of rotation. The tilting element may include means for detachably arranging one end of the tubing segment, however, while at the pump housing means for detachably arranging the other end of the tubing segment are provided. The first end of the tubing segment is thus fixed at the pump housing, while the other end can be moved by pivoting the tilting element.

It is a particular advantage of the stationary first receiving portion that this receiving portion is not lifted or lowered but is fixed to the pump housing so that in this area no pinching of the tube will take place. In this way the risk of hemolysis during the therapy is reduced so that especially during the threading operation before the therapy it is important for the tube not to be badly deformed. Therefore the stationary first receiving portion may be the receiving portion in the direction of which the tube is slightly pushed by the at least one guide pin during threading.

In another embodiment of the tilting element, the latter can be detachably and pivoting arranged on the pump housing by introducing it into a receiving portion at the pump housing forming a pivot bearing for the tilting element, wherein the pivot bearing is disposed in the area of one end of the tubing segment. In this embodiment the tilting element constitutes a separate component which is arranged on the pump housing merely temporarily. The tubing segment and the feeding and discharging lines can be tightly connected to the tilting element which then adopts the function of a multi-connector between the tubing segment and the feeding and discharging lines. The tilting element can also be in the form of a re-usable adapter to which a standard tubing system is mounted merely for therapy. The adapter includes appropriate receiving portions for this purpose.

The axis of rotation of the cover and the pivoting axis of the tilting element can extend normal to each other.

The cover of the pump can have, on its inside facing the respective tilting element in the closed state, a contact surface adjacent to the tilting element and/or the tubing segment in the area of the pivot bearing. The cover can be used to maintain a connector and/or a part of the tubing segment in the area of the axis of rotation of the tilting element in position, when the tilting element is swiveled away from the pump housing. The tilting element and the tubing segment, respectively, thus cannot be detached from the corresponding receiving portion, because the cover presses against them so that the cover thus also has a securing function apart from the function as protection against intervention.

The tilting element may be pivoted to the pump housing about an axis of rotation extending transversely to the axis of rotation of the cover at the pump housing. For example, the axis of the rotation of the cover extends vertically whereas the axis of rotation of the tilting element extends horizontally. The cover then can be simply moved sideward while the inserting and pivoting operation of the tilting element can be performed by ergonomically favorable movements of the hand.

In order to be able to manually move the tilting element by an operator it is accessible at least partly from outside while the cover is closed. When the cover is closed it may be accessible from a side facing the axis of rotation of the cover.

Moreover, it is advantageous when the geometry of the tilting element forms a gripping surface by which the tilting element can be pulled against the closed cover. The geometry of the cover then may form a gripping surface at its respective outside facing away from the tilting element in the closed state, which gripping surface, when the tilting element contacts the cover as counter-bearing, is at a distance from the gripping surface of the tilting element which is larger than 3 mm. When pulling the tilting element against the cover, the operator of the pump thus need not approach his/her fingers more closely than 3 mm, as otherwise this would be uncomfortable and ergonomically unfavorable. This distance therefore may be rather within the magnitude of from 5 mm to 20 mm.

Moreover the geometry of the tilting element and the geometry of the cover can be adjusted to each other so that after pivoting against the closed cover as counter-bearing the tilting element is adjacent with its full surface to a mating surface of the cover. In this way the cover forms a stop which the operator can safely identify as final stop.

In an embodiment of the invention it is further provided that in areas the cover has a hollow bulge in a direction facing away from the pump housing in the closed state of the cover. In the hollow bulge the tubing segment can be located before automated threading or after automated unthreading, after the cover has already been closed. Thus the cover can be closed without the tubing segment being pinched between the rotor and the cover or the height of the pump housing having to be considerably increased so as to provide sufficient space for the tubing segment.

The side contour of the hollow bulge in the closed state of the cover substantially follows the contour of the bearing surface, as in this area an additional space is required for the tubing segment, especially after having been unthreaded. The hollow bulge can flatten in the closed state of the cover toward the tilting element, however.

Furthermore, the invention includes a medical device for extracorporeal blood treatment comprising at least a tube roller pump including a pump housing having a bent bearing surface and a rotor rotating inside the bearing surface, wherein a tubing segment of an extracorporeal blood circulation can be introduced between the bearing surface and the rotor and blood can be fed to the tubing segment via a feeding line, while blood can be discharged from the tubing segment via a discharging line. In accordance with aspects of the invention, the device includes a tube roller pump according to one of the described embodiments.

DESCRIPTION OF THE FIGURES

The invention is best understood from the following detailed description when read in connection with the accompanying drawings. Included in the drawings are the following figures.

DETAILED DESCRIPTION OF THE EMBODIMENTS

Figure 1:
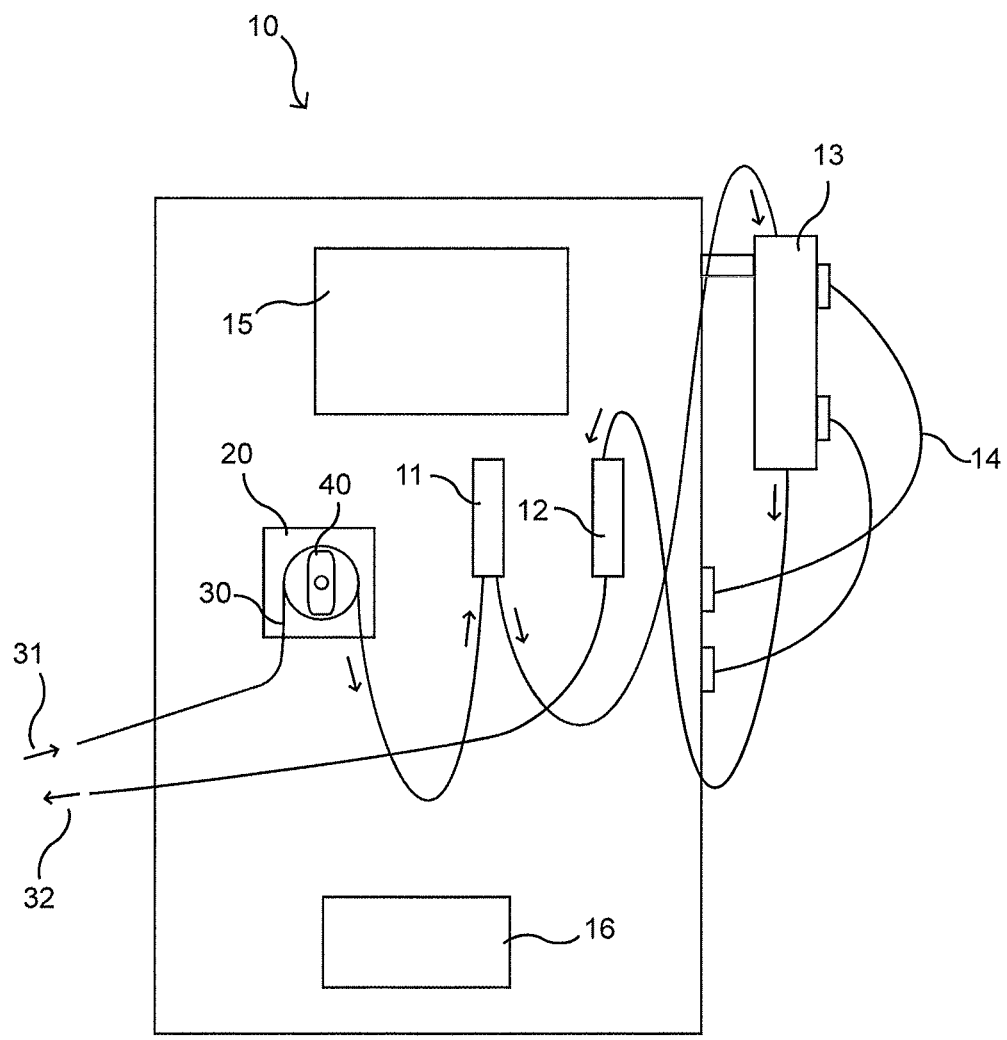
FIG. 1 a schematic representation of a medical device for extracorporeal blood treatment with a blood pump.

FIG. 1 shows a schematic representation of the substantial basic components of a medical device 10 for extracorporeal blood treatment with a blood pump, wherein the blood pump is a tube roller pump. The tube roller pump includes a pump housing 20 that is typically arranged at the front side of the dialyser 10.

To the tube roller pump arterial blood 31 of a patient is fed and delivered through the extracorporeal blood circulation. Subsequently the blood is fed back to the patient as venous blood 32 again. The blood is delivered by means of the pump through a transfer system connected to plural components of the dialyser 10, wherein a tubing segment 30 of the transfer system is inserted in the blood pump and a rotor 40 delivers the blood through the tubing segment 30 in a peristaltic manner, as can be inferred from an enlarged view of FIG. 2.

After passing the blood pump the blood arrives at the dialyser 13 after it may have passed an arterial air trap 11 before. In the dialyser 13 the blood is purified by exchange of substance with a dialysate 14 which is fed to and discharged from the dialyser 13. After passing the dialyser 13 the blood arrives at a venous air trap 12 and is subsequently fed to the patient. This circulation of the patient's blood is marked by arrows in FIG. 1.

Parameters of the dialysis can be adjusted and the therapy can be monitored via a display/input unit 15, which may be in the form of a touchscreen. Furthermore the dialyser 13 includes a control unit 16.

Figure 2:
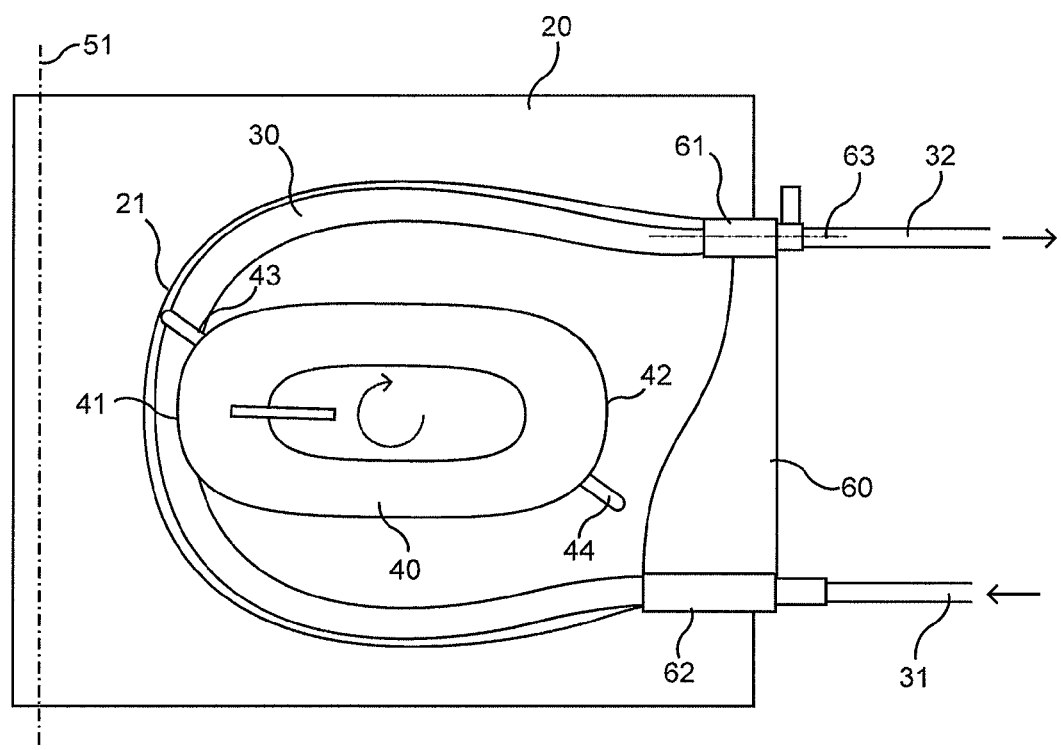
FIG. 2 a schematic top view on a tube roller pump including an inserted tubing piece and a pivotable multi-connector.

FIG. 2 illustrates a schematic representation of a tube roller pump with inserted tubing segment 30 and a first embodiment of a tilting element in the form of a multi-connector 60 to which both the tubing segment 30 and the feeding and discharging lines 31 and 32 of the extracorporeal blood circulation are connected. The tube roller pump includes the pump housing 20 which is easily accessible for the operator of the device, the pump housing 20 being adapted to be covered by a cover 50 (not shown in FIG. 2) which may be pivotable to the left via a pivoting axis 51 so as to get access to the pump.

By an indentation in the housing a curved bearing surface 21 is formed in the pump housing 20 into which bearing surface the tubing segment 30 can be inserted in loop shape so that its two tube ends are protruding from the housing 20. The indentation can be formed to having a side face in the pump housing 20 which extends substantially evenly normal to the front side of the device, or the bearing surface 21 is shaped unevenly by a side face of the indentation which is concave or even twisted in itself.

Inside the bearing surface 21 a rotor 40 having an elliptical circumference is arranged so that it can easily compress the tubing segment 30 during rotation at its vertices 41, 42 or rollers mounted thereon (not shown). By clockwise rotation of the rotor 40 the area of a compressed tubing segment moves equally clockwise, until the corresponding vertex detaches from the tubing segment again. In this period of time the opposed vertex has already contacted the tubing segment 30 again, however, so that in the respective area of the tubing segment 30 in which the latter is compressed by the rotor 40 blood is delivered from the pump inlet to the pump outlet in a peristaltic manner.

At the two ends of the tubing segment 30 the multi-connector 60 is arranged for establishing a connection to a feeding line 31 and a discharging line 32 through which thus blood is fed and discharged. The lines 31, 32 are part of the extracorporeal blood circulation and are connected to different components such as air traps and the dialyzer. The multi-connector 60 is a separate component which can be a fixed part of the disposable so that the multi-connector 60 together with the tubing system can be mounted to be pivoting at the pump. In an alternative embodiment of the multi-connector the latter is in the form of a re-usable adapter on which a standard tubing system can be temporarily arranged so as to be mounted on the pump.

The multi-connector 60 includes a base member interconnecting two opposed connector elements 61 and 62 that can also be referred to as connectors. At least the connector element 61 is cylindrical or has at its outer surface at least a cylindrical area. In this way the connector element 61 can be introduced into an appropriately shaped receiving portion in the pump housing 20, whereby a pivot bearing having an axis of rotation 63 is formed about which the multi-connector 60 is pivotable. The second connector element 62 may be equally cylindrical, wherein it can also be a cylinder having stepped outer surfaces. The cylinder axes of the two connector elements 61, 62 extend in parallel to each other so that the two lines 31, 32 are guided equally in parallel into the pump and out of the pump.

Thus in FIG. 2 the multi-connector 60 can be swiveled out of the plane of projection about the axis of rotation at the connector element 61. In the swiveled in position means are provided for locking the multi-connector 60 at the pump housing 20. For example, to this effect the second connector element 62 is shaped such that it engages in a receiving portion in the pump housing 20 when it is forced against the pump housing 20. However, by slight pulling it can also be released from the receiving portion again, when the multi-connector 10 is swiveled out of the plane of projection of FIG. 2. The base member of the multi-connector 60 therefore may be formed to be slightly elastic so as to allow for engaging in a receiving portion. However, it can also be relatively rigid, wherein the receiving portion in the pump housing 20 would then be elastic.

The surfaces of the multi-connector 60 can have geometrical encodings so as to bring the multi-connector 60 into the correct position at the pump. Furthermore, surfaces can be formed as gripping surfaces by which the multi-connector 60 can be gripped and mounted as easily and ergonomically as possible. To explain the operation of pivoting about the axis of rotation 63 in more detail, each of the FIGS. 3a and 3b illustrates a schematic side view of the tube roller pump with the mounted multi-connector 60 and a cover 50.

Figure 3A:
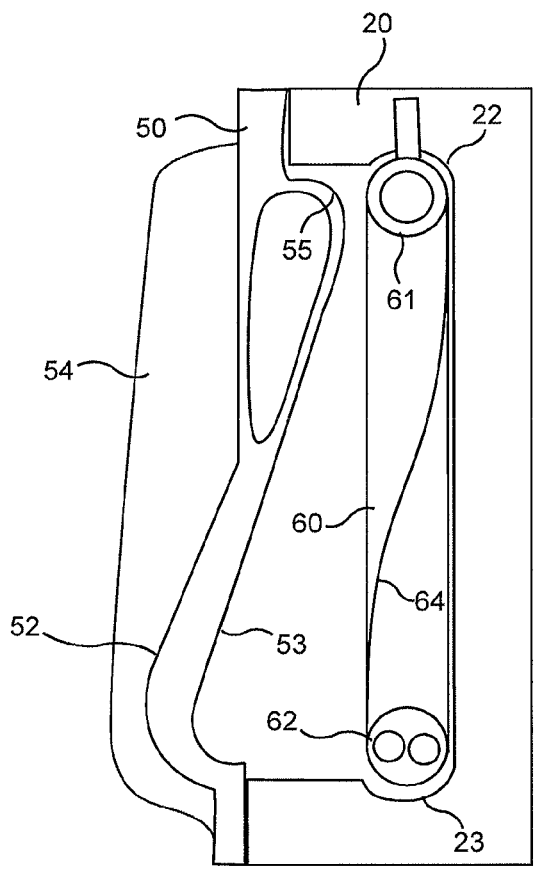
FIG. 3a a schematic side view of a tube roller pump including a closed cover and a multi-connector according to FIG. 2 in the threading position.
Figure 3B:
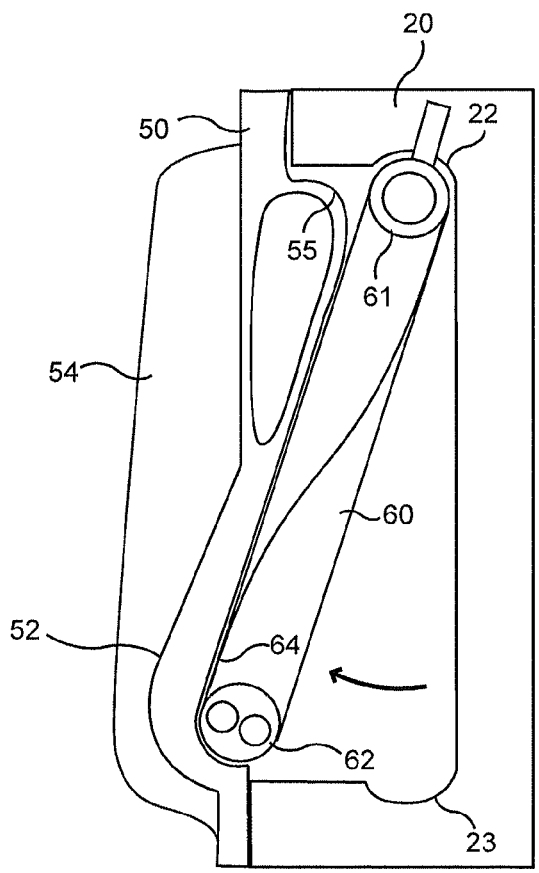
FIG. 3b a schematic side view of a tube roller pump including a closed cover and a multi-connector according to FIG. 2 in the unthreading position.

FIG. 3a illustrates an inserted multi-connector 60 the upper connector element 61 of which is introduced into a semicircular receiving portion 22 in the pump housing 20. The cylindrical shape of the connector element 61 and the receiving portion 20 in this point result in a pivot about which the multi-connector 60 can be pivoted. The lower connector element 62 is equally engaged in a receiving portion. This can be achieved, for example, by a semicircular receiving portion 23 forming a stop mechanism together with the geometry of the multi-connector 60. Also other component parts can be locked, however. The situation shown in FIG. 3a is the therapy position of the multi-connector 60 for which the tubing segment (not shown) arranged on the multi-connector 60 has been threaded in an automated manner. The cover 50 was closed before so as to prevent intervention with the pump during the threading operation and during therapy.

The cover 50 includes a base member the geometry of which forms different functional areas. For example the cover 50 has a bulge 54 and a gripping surface 52 on the outside. On the opposite side of the gripping surface 52 at the inside of the cover 50 a mating surface 53 is formed which is contacted by the multi-connector 60 when the latter is pivoted into the unthreading position. This is illustrated in FIG. 3b. This applies mutatis mutandis to the contact surface 55 in the area of the pivot bearing which contacts the upper area of the multi-connector 60 in the unthreading position and thus prevents the multi-connector 60 from falling out of the upper receiving portion 22.

The gripping surface 52 mainly serves as counter-bearing or operating and actuating surface for actuating the respective tilting element. Although the gripping surface 52 can also be used to open the cover 50, the geometry of the cover 50 is may be configured in the area of the contact surface 55 so that another gripping surface is formed by which the cover 50 can be opened more easily. The gripping surface 56 may be bent slightly outwardly, for instance, as one can infer from the three-dimensional view of FIG. 8.

In order to swivel the lower part of the multi-connector 60 and thus the tubing segment 30 arranged thereto against the cover 50, the user can grip the gripping surface 52 at the cover 50 and the gripping surface 64 at the multi-connector 60 single-handed. He/she can put the thumb, for example, onto the gripping surface 52 of the cover 50 and grip with anyone of other fingers beneath the gripping surface 64 at the multi-connector 60 so that he/she can pull the multi-connector 60 by the fingers against the cover 50 which then constitutes a counter-bearing. This pivoting operation is shown in FIG. 3b by an arrow.

The position of the multi-connector 60 according to FIG. 3b, in which the multi-connector 60 is adjacent to the inside of the cover 50, for the tubing segment 30 arranged thereon constitutes the unthreading position in which one or more guide pins are adapted to lift the tubing segment 30 out of the bearing surface upon rotation of the rotor 40. For maintaining the multi-connector 60 in the unthreading position a spring mechanism can be provided e.g. at the upper pivot bearing. During automated unthreading the cover 50 can remain closed, however, the lifted tubing segment 30 being provided inside the bulge 54 of the cover after unthreading. Subsequently the cover 50 can be opened and the multi-connector 60 can be removed from the pump together with the tubing segment by disengaging the locking in the upper receiving portion 22.

Figure 4:
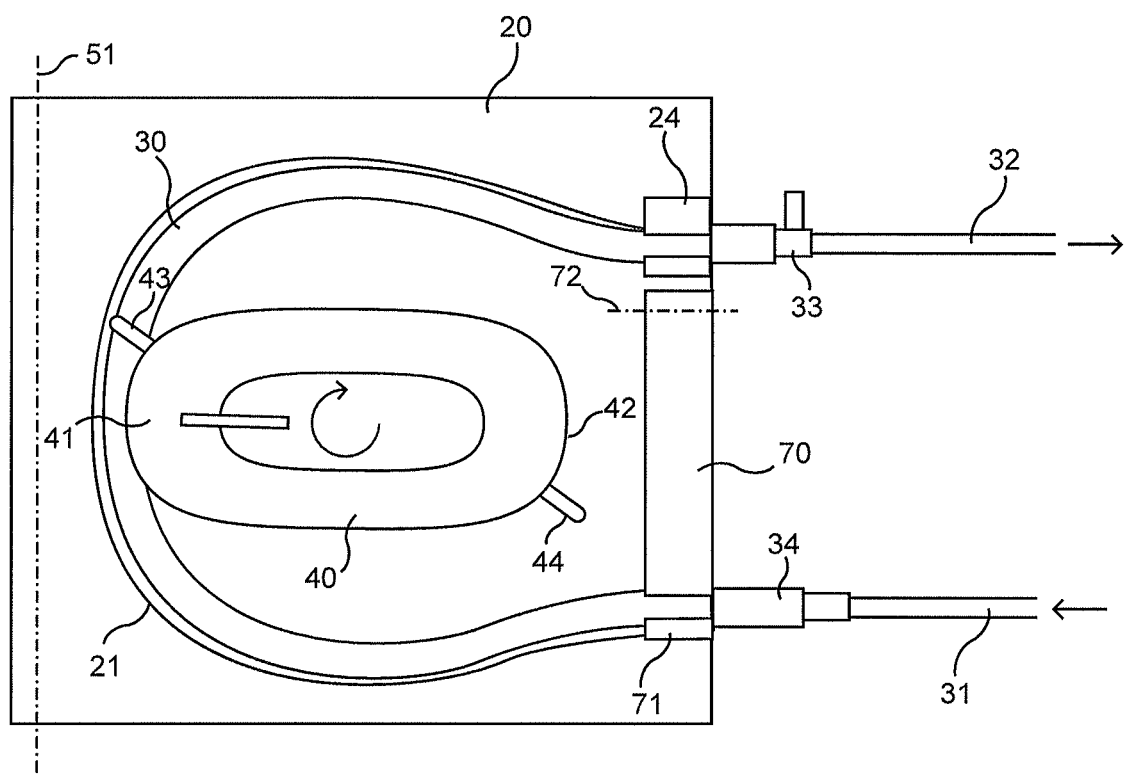
FIG. 4 a schematic top view on a tube roller pump including an inserted tubing piece and a pivotable rocker arm.

FIG. 4 is a schematic representation of a tube roller pump with inserted tubing segment 30 and a second embodiment of a tilting element in the form of a rocker arm 70. The rocker arm 70 is a fixed part of the pump, but the basic structure of the tube roller pump corresponds to the structure already described by way of FIG. 2. However, the tubing segment 30 is connected to a feeding line 31 and a discharging line 32 via individual connecting elements 33 and 34 as it is the case with standard transfer systems. One end of the tubing segment 30 is introduced into a first receiving portion 24 formed in the upper area of the pump housing 20. This receiving portion 24 is fixedly integrated in the pump housing 20 and is configured, for instance, as a hollow cylinder having a longitudinal slit so that the tubing segment 30 can be pressed into the longitudinal slit.

Below the upper (in FIG. 4) receiving portion 24 the rocker arm 70 rotatable about a pivoting axis 72 is arranged. At the pivotable end of the rocker arm 70 a second receiving portion 71 is formed; this can equally be realized by a hollow cylinder having a longitudinal cut. The other end of the tubing segment 30 is pressed into the longitudinal cut. The connectors 33 and 34 are adjacent to the outside of the receiving portions 24 and 71 so that the feeding and discharging lines 31, 32 cannot be drawn into the pump.

Figure 5A:
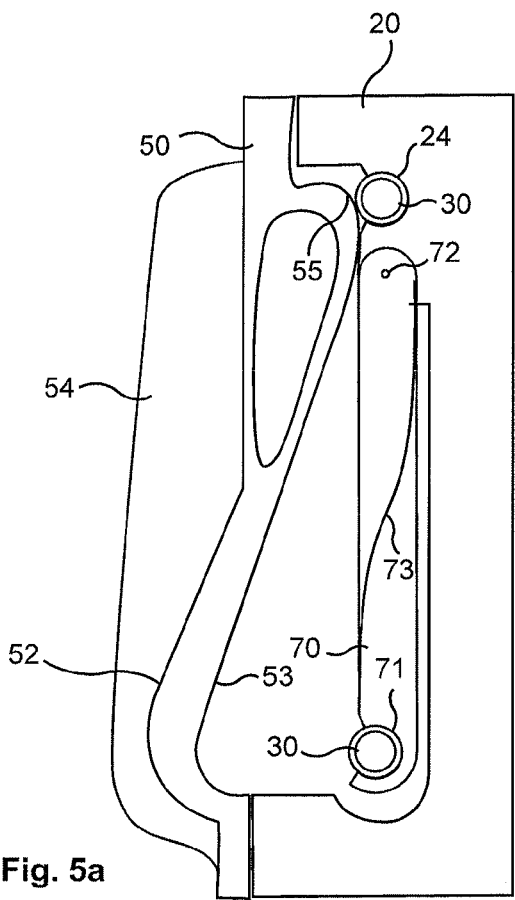
FIG. 5a a schematic side view of a tube roller pump including a closed cover and a rocker arm according to FIG. 4 in the threading position.
Figure 5B:
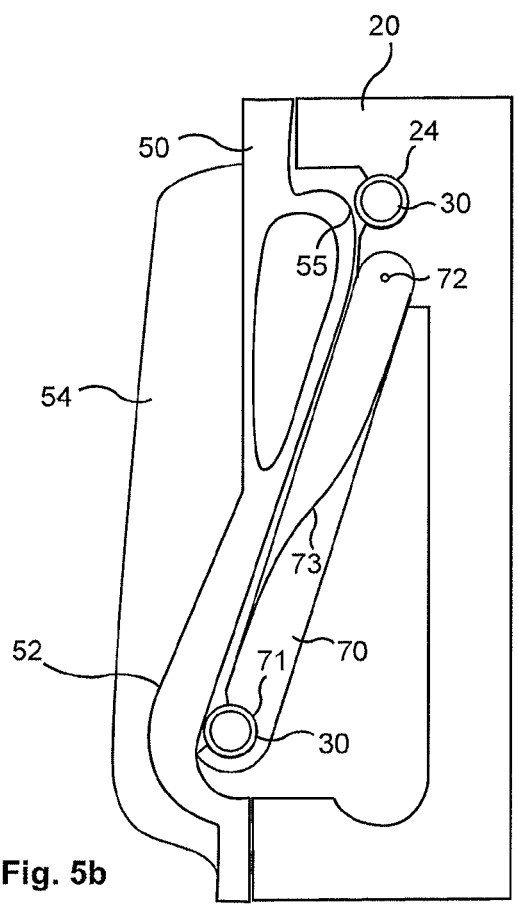
FIG. 5b a schematic side view of a tube roller pump including a closed cover and a rocker arm according to FIG. 4 in the unthreading position.

FIGS. 5a and 5b show the rocker arm 70 analogously to FIGS. 3a and 3b in the therapy position or threading position, respectively, and in the unthreading position in which the lower end of the tubing segment 30 is distanced from the pump bottom so far that a guide pin at the rotor 40 can perform automatic unthreading. The tubing segment 30 is pressed into the upper receiving portion 24 fixed to the pump housing and the other end of the tubing segment 30 is pressed into the lower receiving portion 71 at the rocker arm 70.

A gripping surface 73 can also be formed at the rocker arm 70 so that the latter can be pulled over the axis of rotation 72 toward the closed cover 50. As in the embodiment with the multi-connector this can be done single-handed, the mating surface 53 of the cover 50 again constituting a counter-bearing for the rocker arm 70 in the unthreading position. In this position of FIG. 5b the upper contact surface 55 of the cover 50 may be adjacent to the tubing segment 30 so as to prevent this area of the tubing segment 30 from slipping out of the receiving portion 24. Furthermore in the upper area of the rocker arm 70 another stop mechanism can be provided to maintain the rocker arm 70 in this position.

In both embodiments of the tilting element being a mountable multi-connector 60 or a fixed rocker arm 70 detecting means can be provided to directly detect the position of the respective tilting element in the engaged threading position. The threading position at the same time constitutes the therapy position. After the tilting element has engaged in this position, the cover 50 is closed and the automated threading operation can be started. Detecting means for detecting the state of the cover 50 may also be provided so that the threading operation can be started as soon as it is ensured by the detecting means that the tilting element is in the threading position and the cover is closed.

During threading the rotor 40 is slowly rotated so that the guide pins 41 and 42 carry out the threading operation. At least one guide pin moves outwardly along the tubing segment 30 and forces the same between the rotor 40 and the bearing surface 21. In order to initiate the unthreading operation in the wake of therapy a user pulls the tilting element together with the tubing segment 30 against the cover 50. The cover 50 serves as counter-bearing against which the tilting element can be pulled up to the stop. The stop defines the unthreading position which can equally be detected by detecting means. When the cover 50 is closed and the respective tilting element is in the unthreading position, the rotor 40 can slowly move the guide pins between the pump bottom and the tubing segment 30, thereby the tubing segment 30 being lifted out of the space between the rotor 40 and the bearing surface 21.

Figure 6:
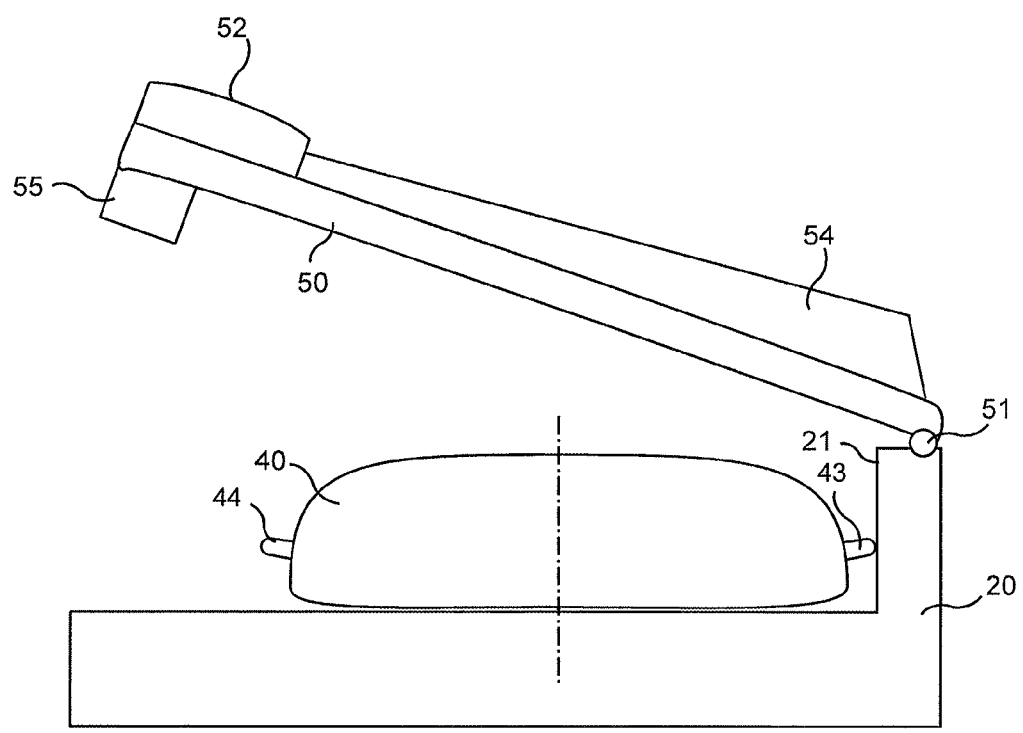
FIG. 6 a schematic section across a tube roller pump with the cover being opened.

FIG. 6 illustrates a schematic section across a tube roller pump with the cover being slightly opened, the cover 50 being pivoted forward about the axis of rotation 51 and no tubing segment having been inserted yet. It can also be taken from this view that the bulge 54 at the outside of the cover 50 may flatten in the direction of the gripping surface 52, as the space of the bulge 54 has to be largest in the other direction so as to accommodate the tubing segment before threading or after unthreading.

Figure 7A:
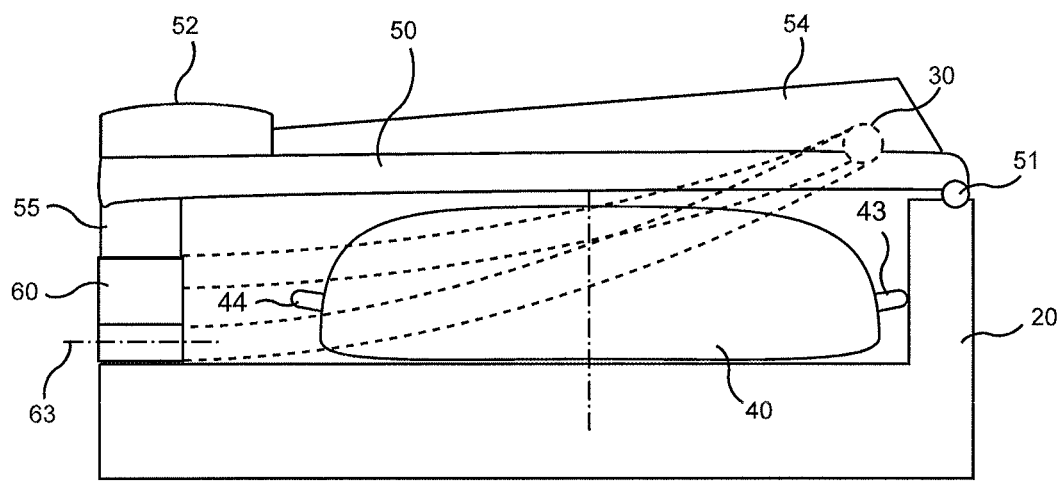
FIG. 7a a schematic cross-section according to FIG. 6 before the threading operation or after the unthreading operation.

FIG. 7*a* illustrates the cross-section of the tube roller pump with a closed cover 50, the tubing segment 30 by way of example being disposed at a multi-connector 60 adjacent to the cover 50 in the unthreading position. Since this is a top view, the schematic representation of FIG. 7*a* also shows that the upper contact surface 55 of the cover 50 contacts the upper connector of the multi-connector 60. The tubing segment 30 extends inside the pump housing 20 and the bulge 54 in the cover 50, the course of the tubing segment 30 being shown in broken lines. To be able to lift the tubing segment 30 into the position, at least one guide pin 43, 44 has moved between the tubing segment 30 and the bottom of the pump housing 20 upon rotation of the rotor 40.

Figure 7B:
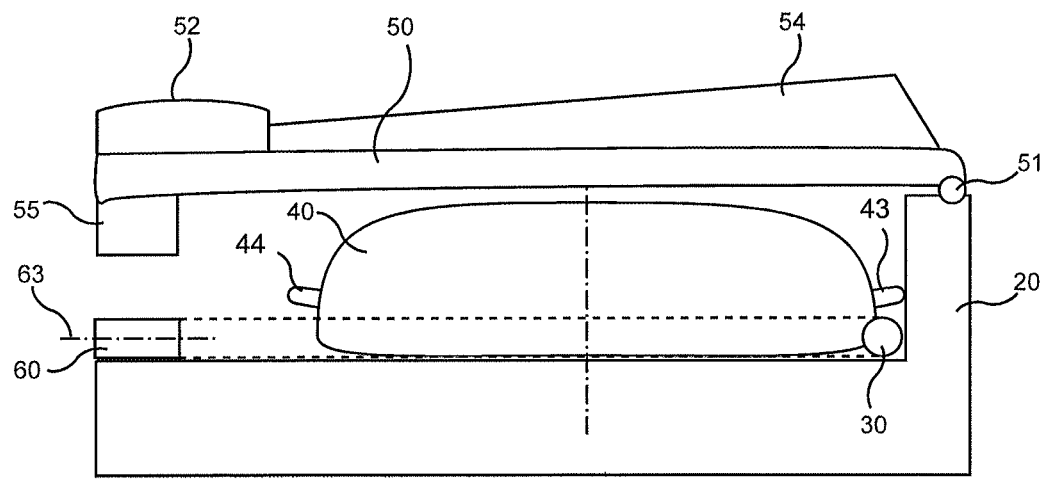
FIG. 7b a schematic cross-section according FIG. 6 during therapy.

FIG. 7*b* illustrates the cross-section of the tube roller pump with a closed cover 50, the multi-connector 60 having been brought into the threading position and the tubing segment 30 being threaded already between the rotor 40 and the bearing surface 21. So that the tubing segment 30 can be threaded into this position at least one guide pin 43, 44 has moved between the tubing segment 30 and the cover 50 upon rotation of the rotor 40.

Figure 8:
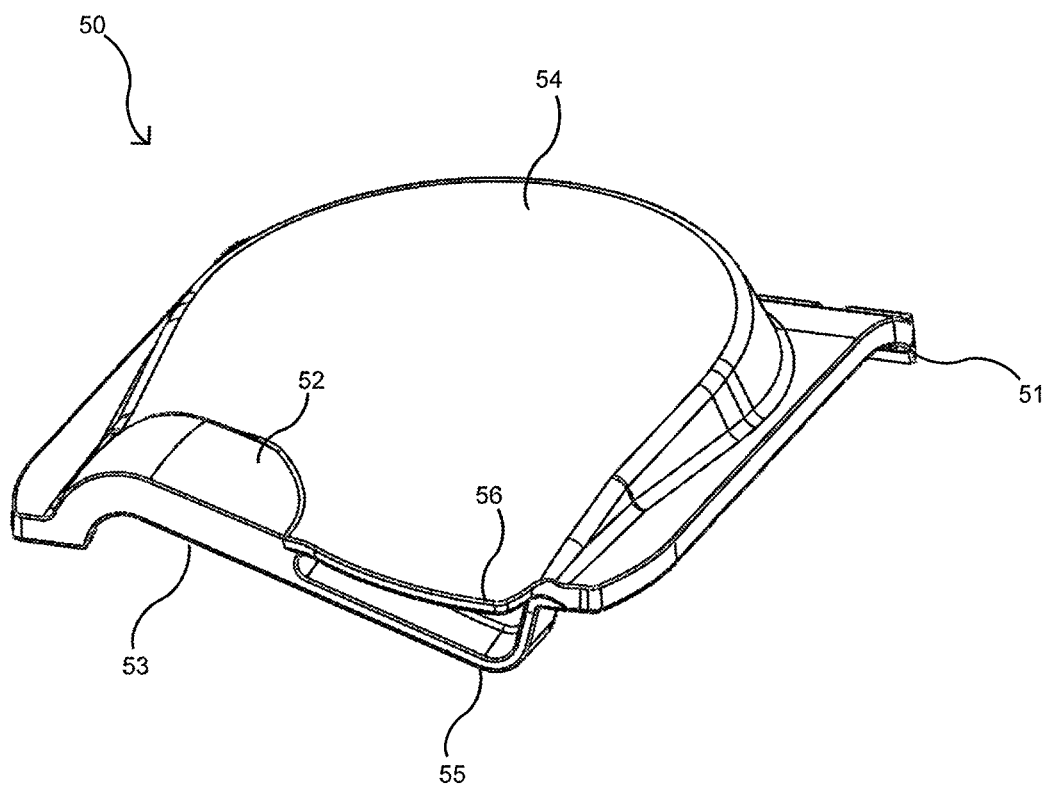
FIG. 8 a three-dimensional view of the cover.

Moreover, FIG. 8 illustrates a three-dimensional view of the cover 50 including the hollow bulge 54 and the outer gripping surface 52. On the opposite side of the gripping surface 52 the mating surface 53 is formed and the contact surface 55 is formed by a hollow thickening in this area. In the area of the contact surface 55 the cover forms the gripping surface 56 for opening the cover 50 on the opposite side. It is further evident in which way the bulge 54 flattens in the direction of the gripping surface 52.

The invention claimed is:

1. A tube roller pump for a medical device for extracorporeal blood treatment comprising a pump housing having a bent bearing surface and a rotor rotatable inside the bearing surface, wherein a tubing segment can be introduced between the bearing surface and the rotor in loop shape and at the pump housing means for arranging the tubing segment are provided by which at least one end of the tubing segment can be arranged at the pump housing so as to be pivotable about an axis of rotation, wherein the tubing segment can be pivoted by pivoting a tilting element on which the tubing segment is at least partly mounted, wherein a cover is pivotably arranged on the pump housing and can at least partly cover the pump housing, the cover being formed and arranged at the pump housing so that in the closed state upon pivoting the tubing segment in the direction of the closed cover it constitutes a counter-bearing for the tilting element by which the tubing segment mounted thereon can be aligned at a defined position relative the pump housing, and the tube roller pump includes at least means for automated unthreading of the tubing segment from the bearing surface at the defined position.

2. The tube roller pump according to claim 1, wherein the tilting element is a fixed component of the tube roller pump and includes means for detachably arranging at least one end of the tubing segment.

3. The tube roller pump according to claim 2, wherein the tilting element includes means for detachably mounting one end of the tubing segment, whereas means for detachably mounting the other end of the tubing segment are provided at the pump housing.

4. The tube roller pump according to claim 1, wherein the tilting element is adapted to be detachably and movably mounted on the pump housing by being adapted to be introduced into a receiving portion at the pump housing which forms a pivot bearing for the tilting element, the pivot bearing being arranged in the area of one end of the tubing segment.

5. The tube roller pump according to claim 1, wherein the cover includes at its inside, which faces the tilting element in the closed state, a contact face which contacts the tilting element and/or the tubing segment in the area of the pivot bearing.

6. The tube roller pump according to claim 1, wherein the tilting element is arranged at the pump housing so as to be pivotable about an axis of rotation extending transversely to the axis of rotation of the cover at the pump housing.

7. The tube roller pump according to claim 1, characterized in that, when the cover is closed, the tilting element is accessible at least partly from outside.

8. The tube roller pump according to claim 7, wherein the geometry of the tilting element forms a gripping surface by which the tilting element can be pulled against the closed cover.

9. The tube roller pump according to claim 8, wherein at its outside facing away from the tilting element in the closed state the geometry of the cover forms a gripping surface which when the tilting element contacts with the cover as a counter-bearing is at a distance from the gripping surface of the tilting element which is larger than 3 mm.

10. The tube roller pump according to claim 1, wherein the geometry of the tilting element and the geometry of the cover are adjusted to each other so that, after pivoting against the closed cover as a counter-bearing, the tilting element is adjacent with its full surface to a mating surface of the cover.

11. The tube roller pump according to claim 1, wherein the cover in portions has a hollow bulge in a direction facing away from the pump housing in the closed state of the cover.

12. The tube roller pump according to claim 11, wherein the side contour of the hollow bulge in the closed state of the cover substantially follows the contour of the bearing surface.

13. The tube roller pump according to claim 11, wherein the hollow bulge in the closed state of the cover flattens in the direction of the tilting element.

14. A medical device for extracorporeal blood treatment comprising at least the tube roller pump of claim 1, wherein the tubing segment is of an extracorporeal blood circulation and blood can be fed to the tubing segment via a feeding line, while blood can be discharged from the tubing segment via a discharging line.

* * * * *